United States Patent
Lumme et al.

(10) Patent No.: US 10,849,556 B2
(45) Date of Patent: Dec. 1, 2020

(54) SOLUTION FOR FORM-FITTING STRAP

(71) Applicant: Polar Electro Oy, Kempele (FI)

(72) Inventors: Lauri Lumme, Oulu (FI); Olli Komulainen, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 218 days.

(21) Appl. No.: 15/740,137

(22) PCT Filed: Jun. 29, 2015

(86) PCT No.: PCT/EP2015/064702
§ 371 (c)(1),
(2) Date: Dec. 27, 2017

(87) PCT Pub. No.: WO2017/000980
PCT Pub. Date: Jan. 5, 2017

(65) Prior Publication Data
US 2018/0192954 A1     Jul. 12, 2018

(51) Int. Cl.
*A61B 5/00* (2006.01)
*A61B 5/11* (2006.01)
(Continued)

(52) U.S. Cl.
CPC .......... *A61B 5/6831* (2013.01); *A61B 5/0205* (2013.01); *A61B 5/1118* (2013.01);
(Continued)

(58) Field of Classification Search
CPC ....... A61B 5/68; A61B 5/6801; A61B 5/6802; A61B 5/681; A61B 5/6813; A61B 5/6824; A61B 5/6825; A61B 5/6826; A61B 5/6828; A61B 5/683; A61B 5/6831; A61B 5/6843; A61B 5/6879; A61B 5/6882; A61B 5/6884; A61B 5/6885; A61B 5/02; A61B 5/0205; A61B 5/02055; A61B 5/021; A61B 5/022; A61B 5/0225; A61B 5/024; A61B 5/02416
(Continued)

(56) References Cited

U.S. PATENT DOCUMENTS 10,149,521 B2 * 12/2018 Baranski ............... A44C 5/0069
2016/0066842 A1 * 3/2016 Kokkoneva .......... A61B 5/6885
                                                                 600/479
(Continued)

FOREIGN PATENT DOCUMENTS

WO    WO2014117125 A1    7/2014

OTHER PUBLICATIONS

L. Leonard, "Portable, Shape-Changing Digital Device Bracelets with Color Electrophoretic Displays", Retrieved from the Internet: URL:http:marblar.com/idea/7oDPq, pp. 1-6, Nov. 20, 2013.
(Continued)

*Primary Examiner* — Ahmed M Farah
(74) *Attorney, Agent, or Firm* — FisherBroyles, LLP

(57) ABSTRACT

An apparatus includes a band configured to attach a physical activity measurement device to a human body, and electroactive material comprised in the band. The electroactive material is configured to change at least one of size and shape of the band in response to an electric input from the physical activity measurement device to the electroactive material.

20 Claims, 7 Drawing Sheets

(51) Int. Cl.
*A61B 5/0205* (2006.01)
*A61B 5/024* (2006.01)

(52) U.S. Cl.
CPC .......... *A61B 5/02416* (2013.01); *A61B 5/681* (2013.01); *A61B 5/6824* (2013.01); *A61B 2560/0209* (2013.01); *A61B 2562/0219* (2013.01)

(58) Field of Classification Search
USPC ........ 600/301, 309–311, 371, 382, 384, 386, 600/390
See application file for complete search history.

(56) References Cited

U.S. PATENT DOCUMENTS

| | | | | |
|---|---|---|---|---|
| 2016/0151669 | A1* | 6/2016 | Komulainen | A61B 5/1118 702/160 |
| 2016/0187977 | A1* | 6/2016 | Cruz-Hernandez | G06F 3/016 345/156 |
| 2016/0204332 | A1* | 7/2016 | Hunt | H04M 1/05 318/16 |
| 2016/0256741 | A1* | 9/2016 | Holma | G06F 19/3481 |
| 2017/0065224 | A1* | 3/2017 | Rahko | A61B 5/7435 |
| 2017/0119314 | A1* | 5/2017 | Just | A61B 5/6816 |
| 2017/0157466 | A1* | 6/2017 | Korpela | A61B 5/0205 |
| 2017/0340209 | A1* | 11/2017 | Klaassen | A61M 27/00 |
| 2018/0092550 | A1* | 4/2018 | Sprenger | A61B 5/02225 |
| 2018/0338721 | A1* | 11/2018 | Wang | A61B 5/6814 |

OTHER PUBLICATIONS

International Search Report for corresponding International Application No. PCT/EP2015/064702, pp. 1-4, dated Feb. 24, 2016.
Written Opinion for corresponding International Application No. PCT/EP2015/064702, pp. 1-7, dated Feb. 24, 2016.

* cited by examiner

SOLUTION FOR FORM-FITTING STRAP

CROSS-REFERENCE TO RELATED APPLICATION

This application is a National Stage application of International Application No. PCT/EP2015/064702, filed Jun. 29, 2015, which is incorporated by reference herein in its entirety.

BACKGROUND

Field

The invention relates to a strap for attaching an electronic device to a part of a body, e.g. to a wrist.

Description of the Related Art

An electronic device such as a wrist watch or a physical activity measurement device may be attached to a human body, e.g. the wrist, with a strap. Conventionally, the function of the strap has been to prevent the electronic device from falling off. For that purpose and for the convenience of the user, the strap often has an adjustable mechanism which helps in finding the suitable compromise between the above-mentioned function and the convenience for the user. Typically, the user adjusts the strap such that the strap is not pressed very tightly around the wrist. However, in some use scenarios, it is advantageous to attach the strap more tightly than what is customary for the user.

SUMMARY

The invention is defined by the subject matter of the independent claim. Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

Figure 1:
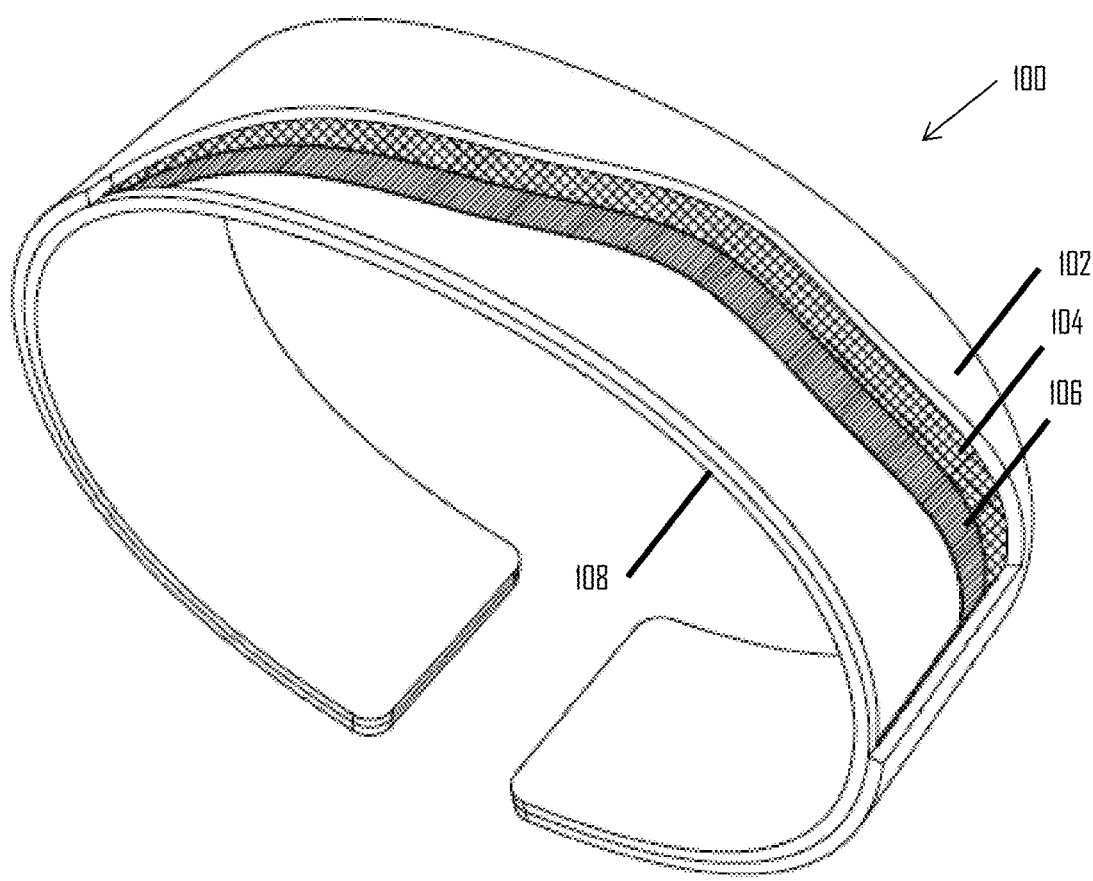
FIG. 1 illustrates a band suitable for attaching a physical activity measurement device to an object according to an embodiment of the invention.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Embodiments of the invention relate to a physical activity measurement device attachable to an object such as a human body for use during a physical exercise and/or during daily routines. Such embodiments may employ the physical activity measurement device to measure physiological training data from the user's performance during the physical exercise and to output the training data to the user via a user interface of the physical activity measurement device and/or via a user interface of another apparatus. The physical activity measurement device may employ one or more biometric sensors. One example of the biometric sensor is a heart activity sensor. The physical activity measurement device may employ other sensor as well, such as an acceleration sensor, a satellite positioning receiver, and/or sensors applicable to training equipment such a bicycle or gym equipment. The physical activity measurement device may be configured to measure physiological parameters from the user not only during the physical exercise but also during daily activities and routines of the users. The present invention is applicable to physical activity measurement devices such as activity monitoring devices, training computers, etc.

Some embodiments of the invention relate to an apparatus arranged to attach the physical activity measurement device to the object. Such an apparatus may comprise an attachment structure designed and arranged to receive the physical activity measurement device in a fixed, integrated, or detachable manner and to attach the physical activity measurement device to the object. The attachment may be realized by a band that may be designed to encircle the object such that the band is attached around the object. The band may comprise locking parts at ends of the band where the locking parts form mutually counterparts such as a buckle and a catch. The locking parts may fix the band around the object as is commonly known in the field of wristwatches, wrist computers etc.

The band may be made of flexible material such that it conforms to the dimensions of the object when placed around the object or into contact with the object, e.g. around a wrist, finger, auricle, or foot, or into an ear canal. Conventional materials of the band include silicone, leather, and textile.

Electroactive polymers are polymers that exhibit a change in size or shape when stimulated by an electric field or an electric input. Known applications of this type of material include actuators and sensors. A typical characteristic property of an electroactive polymer is that it can undergo a large amount of deformation in response to the electric input. Electroactive polymers include dielectric electroactive polymers that are materials in which the change of size or shape is caused by electrostatic forces between two electrodes which squeeze the polymer. Dielectric electroactive polymers are capable of very high strains and may be considered as a capacitor that changes its capacitance when a voltage is applied by allowing the polymer to compress in thickness and expand in area due to the electric field. This type of electroactive polymer may require a relatively high actuation voltage to produce high electric fields (e.g. hundreds or thousands of volts), but very low electrical power consumption. Dielectric electroactive polymers require no power to keep a given position. Examples of dielectric electroactive polymers include electrostrictive polymers and dielectric elastomers. Ionic electroactive polymers are materials in which deformation is caused by displacement of ions inside the polymer. Only a few volts may be needed for the deformation, but the ionic flow implies that electrical power is needed for maintaining the deformation, and energy is needed to keep the material at a given position. Examples of the ionic electroactive polymers include conductive polymers, ionic polymer-metal composites, and responsive gels. Yet another example is a Bucky gel actuator, which is a polymer-supported layer of polyelectrolyte material consisting of an ionic liquid sandwiched between two electrode layers consisting of a gel of ionic liquid containing single-wall carbon nanotubes.

Referring to FIG. 1, let us describe an embodiment of the invention in the form of an apparatus comprising a band 100 configured to attach a physical activity measurement device to a human body. FIG. 1 illustrates a cut-out view of the band 100 such that inner contents of the band are visible. The apparatus further comprises electroactive material 106 coupled to the band 100 or comprised in the band 100, wherein the electroactive material 106 is configured to change in at least one of size and shape in response to an electric input from the physical activity measurement device to the electroactive material 106.

The electroactive material 106 may be integrated into the band 100, e.g. enclosed inside silicone layer(s) 102, 108 that form surfaces of the band 100. In other embodiments, the electroactive material 106 is attached to an inner surface of the band 100, wherein the inner surface may be understood as the surface that faces the object to which the band 100 attaches the physical activity measurement device. The electroactive material 106 may comprise any one of the above-described electroactive materials, e.g. electroactive polymers. An electrode 104 may be coupled to the electroactive material to form an electrode 104 electrically coupled to the physical activity measurement device in order to receive the electric input from the physical activity measurement device. In an embodiment, the electroactive material is provided between two electrodes such that the electric input causes an electric field over the electroactive material which causes the electroactive material 106 to change in size and/or shape.

In an embodiment, the electroactive material 106 is arranged such that it expands, as a response to the electric input, into a direction perpendicular to the inner surface of the band 100. In particular, the electroactive material 106 expands towards the object when the band 100 is attached to the object. Accordingly, the expansion reduces the effective circumference of the band 100 and causes the band to tighten around the object more firmly. The reduction may be in an inner circumference of the band 100, the inner referring to the surface or side of the band that faces the object when the band 100 is attached to the object. The degree of the expansion and, as a consequence, of the compression of the band to the object may be defined by the electric input. A higher voltage or current of the electric input may cause a higher expansion towards the object and, thus, higher compression. Accordingly, the band attaches the physical activity measurement device around the body in a form-fitting manner. The form-fitting of the band is provided particularly in areas of the electroactive material.

Figure 2A:
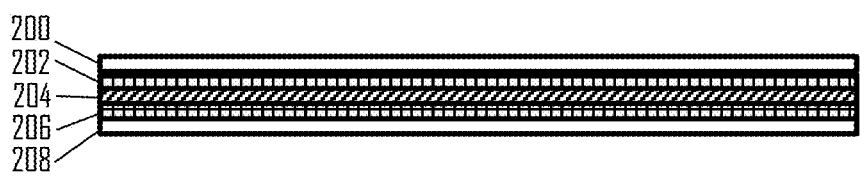
FIGS. 2A and 2B illustrate layers of the band according to an embodiment of the invention in a default and deformed position.
Figure 2B:
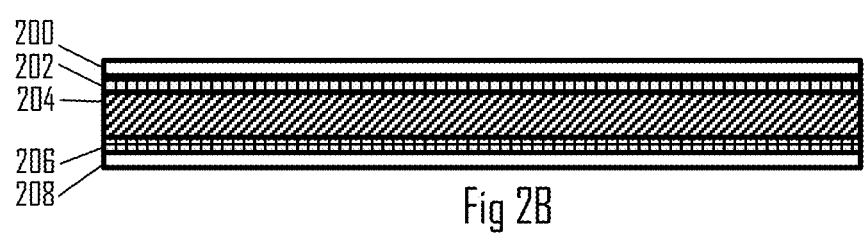

FIGS. 2A and 2B illustrate an embodiment of the invention where the electroactive material may be material that changes in volume in response to the electric input. Such a material may be the above-described ionic gel, for example. Referring to FIG. 2A, the band 100 may comprise a first surface layer 200 and a second surface layer 208 on opposite surfaces of the band 100. Electrode layers 202, 206 may be provided between the surface layers 200, 208, and the electrode layers may be electrically coupled to the physical activity measurement device. In an embodiment, the electrode layers comprise conductive powder, e.g. graphite powder. An electrode may be attached to each electrode layer, and signal lines may couple the electrodes electrically to the physical activity measurement device. An electroactive material layer 204 may be provided between the electrode layers, wherein the electroactive material layer 204 may comprise the material that changes in volume in response to the electric input. FIG. 2A illustrates the layers in a situation where no electric stimulus is applied to the electrode layers 202, 206, and FIG. 2B illustrates the layers in a situation where the electric stimuli is applied to the electrode layers 202, 206. In response to the electric stimuli, the electroactive material expands in volume and in thickness of the layer and, as a consequence, compresses the band more tightly to the object when the band is fixed around the object.

The embodiment of FIGS. 2A and 2B may be realized by embedding particles of electroactive material into the material of the band, e.g. in silicone material, plastics material, or rubber material of the band. The electrodes may be formed into top and bottom surfaces of the band 100, and a protective coating may be provided on top of the electrodes. The coating may comprise the same band material, with or without the particles of the electroactive material.

In an embodiment, the elasticity of the inner surface 208 of the band is higher than the elasticity of the outer surface 200. In other words, the outer surface 200 may be more rigid than the inner surface 208. As a consequence, the band may direct the deformation of the electroactive material more towards the inner surface and towards the object.

Figure 3A:
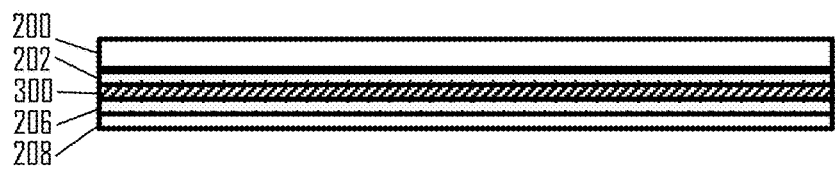
FIGS. 3A, 3B, and 3C illustrate layers of the band according to another embodiment of the invention in a default and deformed position.
Figure 3B:
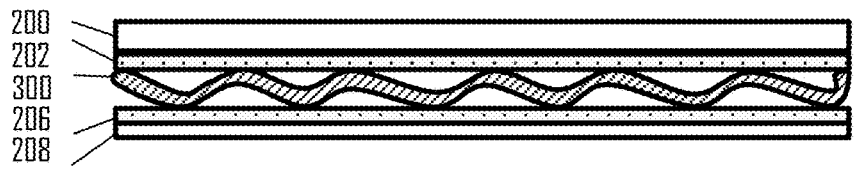

FIGS. 3A and 3B illustrates an embodiment where the electroactive material layer 300 comprises electroactive material that changes in the shape but not necessarily in size or volume. The electroactive material may be dielectric electroactive polymer, for example. The other layers 200, 202, 206, 208 may be the same as in the embodiment of FIGS. 2A and 2B. In this embodiment, the electric input from the physical activity measurement device may cause an electric field through the electroactive material 300 that causes the electroactive material to bend such that the bending causes displacement of the layers 206, 208 with respect to the layers 200, 202. In particular, the layers 206, 208 may withdraw with respect to the layers 200, 202, thus resulting in increase of an effective thickness of the band 100 and decrease of the effective circumference of the band. As a consequence, the band compresses to the object when placed around the object, wherein the degree of the compression is defined by the deformation of the electroactive material in the direction perpendicular to the inner surface of the band 100.

Figure 3C:
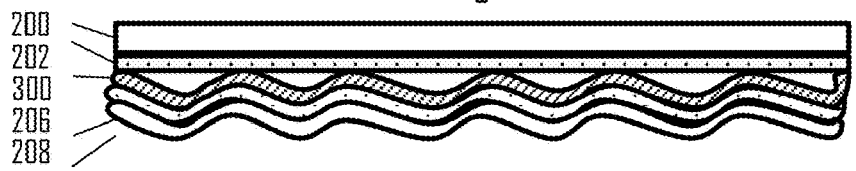

FIG. 3C illustrates an embodiment where layers 206 and 208 are attached to the electroactive material 300 such that they deform along with the electroactive material in response to the electric input. The deformation of the layers 208, 208 may comply with the deformation of the electroactive material 300 because of the attachment.

Figure 4:
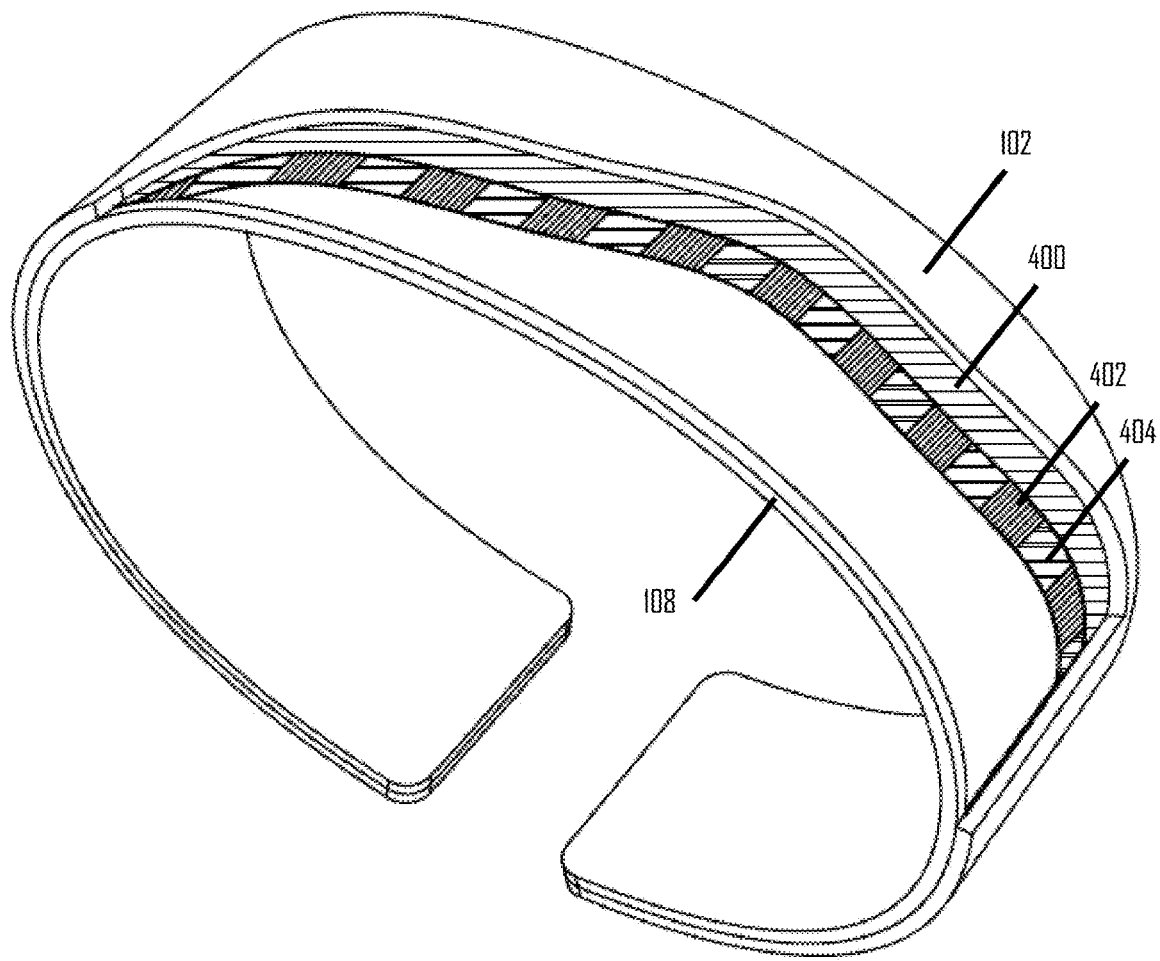
FIG. 4 illustrates an embodiment of the band where electroactive material is provided in modules.

FIG. 4 illustrates an embodiment where the electroactive material is arranged in a plurality of modules 402. Each module may be provided between two electrode modules 404. The electrode modules may comprise the same material as the electrode layers 202, 206 of FIGS. 2A and 2B, e.g. the conductive powder. Concatenated modules of the electroactive material and the electrode modules may be provided between the electrode layers 202, 206, as illustrated in FIG. 5A, or the electrode layers 202, 206 may be omitted in this embodiment because the electrode module serve the same or similar purpose.

Figure 5A:
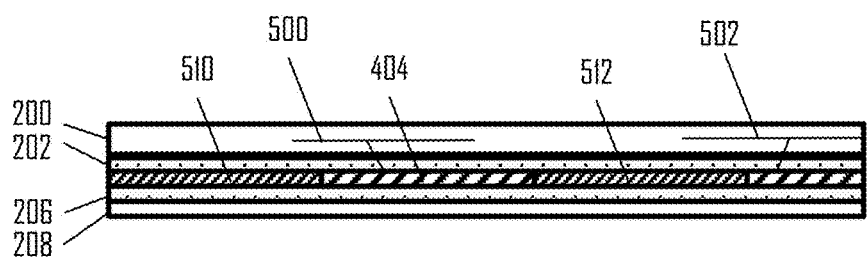
FIGS. 5A and 5B illustrate the modular structure of the electroactive material in a default and deformed position.
Figure 5B:
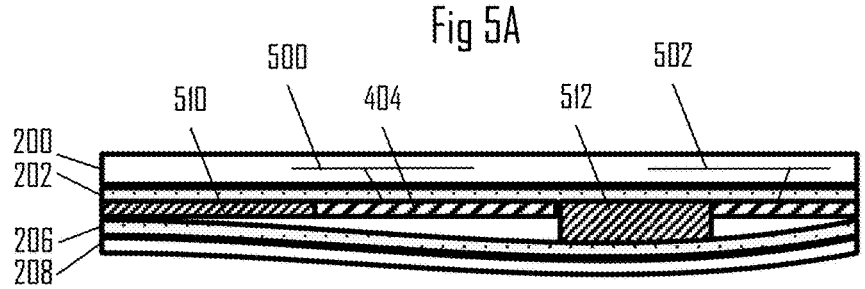

Referring to FIGS. 5A and 5B, the modular structure enables that each module may be controlled independently. Accordingly, a separate electric coupling 500, 502 may be provided for each electrode module 404. A dedicated signal line may be provided from the physical activity measurement device to each module in order to realize the separate electric coupling. When the target is to change the shape and size of the electroactive module 512, the electric input may be applied from the physical activity measurement device to the electrodes adjacent to the electroactive module 512. This causes the electroactive material to change in the size and/or shape. The modular structure is applicable directly to all embodiments of FIGS. 2A, 2B, 3A, 3B. Independent control provides more options as how to adjust the form-fitting of the band 100.

FIG. 5B illustrates an embodiment where the electric input is to the module 512 but not to the adjacent module 510. The electric input causes the module 512 to expand such that form-fits the band to the object more in the area of the module than in the area of the module 510. This embodiment allows bringing the area of the module into better contact with the user's skin. Such an embodiment may be advantageous in an application where a sensor needs to be brought into close contact with the skin. The sensor may be an optic heart activity sensor, for example. Various other applications may, however, may be envisaged. Depending on the number and layout of the modules, the band may be deformed into various shapes by different electric inputs output to the modules.

Figure 6:
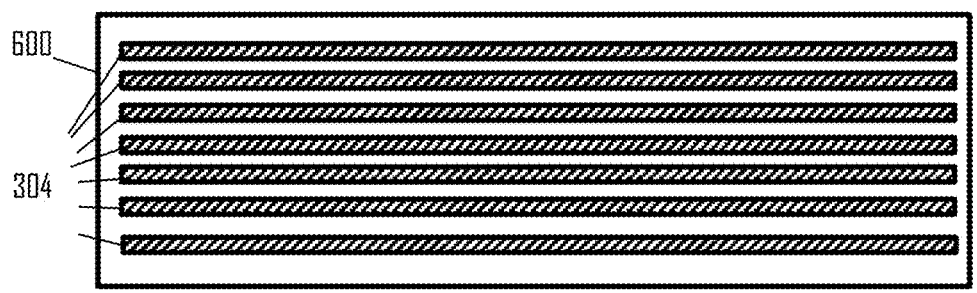
FIG. 6 illustrates an embodiment where the electroactive material is provided in the band in strips.

In the embodiment of FIGS. 5A and 5B, the modular structure is realized by providing a concatenated set of modules along a longitudinal axis of the band 100. In another embodiment illustrated in FIG. 6, the modules are arranged in the form of a plurality of parallel strips of electroactive material 304 arranged along a lateral axis of the band 600. The strips may extend along the longitudinal axis of the band 600. The electrode modules (not shown) may be provided between the strips such that an interleaved structure of electroactive material modules 304 and electrode modules is provided when viewed along the lateral axis of the band 600. This embodiment may provide a good control of the expansion of the electroactive material in the direction away from the plane of the band 600.

In general, the expansion of the electroactive material to a desired direction may be controlled by the design and layout of the electroactive material (modules). The expansion may be controlled by providing support structures in the band 100, 600 that direct the expansion of the electroactive material to the desired direction. The support structures may be rigid or substantially rigid such that they affect the direction to which the electroactive material expands.

In an embodiment, the apparatus comprises the band 100, 600 without the physical activity measurement device. The band, 600 100 may comprise a housing or a receptable for the physical activity measurement device. In such embodiments, the band 100 may be replaceable.

Figure 7A:
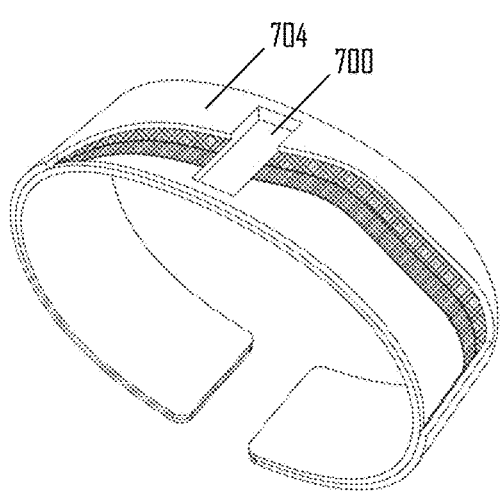
FIG. 7A illustrates an embodiment where the band comprises a housing for a casing containing electronics according to an embodiment of the invention.
Figure 7B:
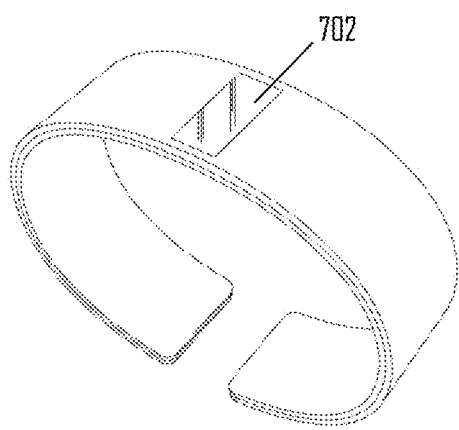
FIG. 7B illustrates an embodiment comprising the band and a physical activity measurement device.

In other embodiments, the apparatus comprises the physical activity measurement device attached to the band 100, 300 in a fixed or detachable manner. FIGS. 7A and 7B illustrate an embodiment of such an apparatus. Referring to FIG. 7A, the band may comprise a receptable or a housing 700 for a casing of the physical activity measurement device. The receptable may be arranged in the band as a hole, recession, or a through hole such that the receptable penetrates at least the first surface layer 704 (or surface layer 200), thus enabling the physical activity measurement device to contact electrically with the electrode(s) or electrode layers of the band. In FIG. 7B, the casing of the physical activity measurement device 702 is attached to the band. A display of the device 702 may be arranged as visible to the user, as shown in FIG. 7B.

Figure 8:
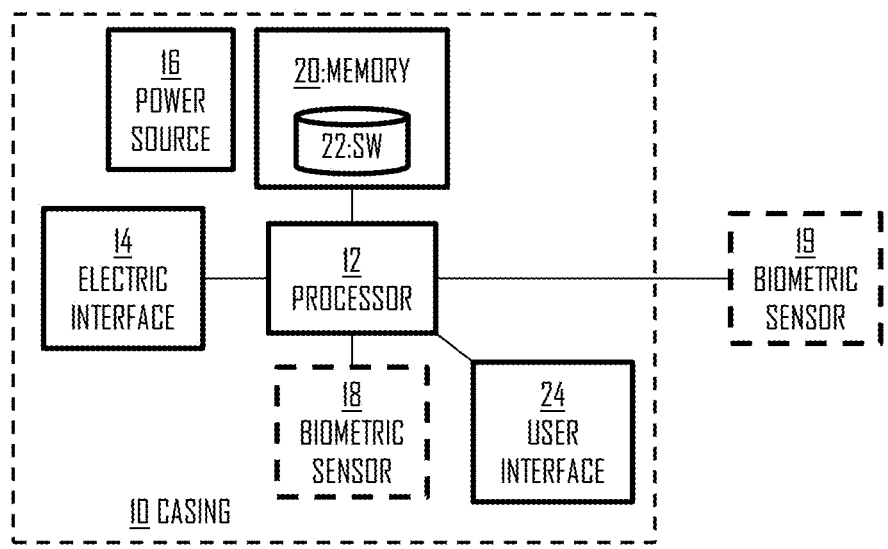
FIG. 8 illustrates a block diagram of a physical activity measurement device according to an embodiment of the invention.

Let us now describe an embodiment of the physical activity measurement device with reference to FIG. 8. FIG. 8 illustrates an embodiment of structural components of the physical activity measurement device. At least some of the structural components may be provided in the same casing 10 or, in some embodiments, all the components of the physical activity measurement device are provided in the same casing 10. The physical activity measurement device may comprise a power source 16 which may provide the physical activity measurement device with electric power supply. The power source 16 may comprise a battery. In some embodiments, the power source may be external such as mains, a power source of an external computer connected to the physical activity measurement device via an interface such as universal serial bus (USB), or another external power source.

The physical activity measurement device may further comprise at least one processor 12 or a processing circuitry configured to control the operations of the physical activity measurement device. The operation of the processor 12 may be defined by one or more computer program modules 22 stored in a memory 20 of the physical activity measurement device. Upon reading a computer program module from the memory 20, the processor may execute a computer process comprising technical functions defined by the computer program module. At least some of the technical functions may comprise controlling the electric output to control the deformation of the electroactive material, as described herein. The memory may further store measurement data acquired during the operation of the physical activity measurement device. The measurement data may comprise biometric measurement data and/or measurement data acquired during a physical exercise performed by the user of the physical activity measurement device. The measurement data may be acquired when the processor 12 operates in a measurement mode.

The physical activity measurement device may in some embodiments comprise at least one biometric sensor 18. The biometric sensor may comprise any one of the following: a heart activity sensor, an optical heart activity sensor, a blood pressure sensor, and a pulse oximetry sensor. The optical heart activity sensor may be based on measuring a photoplethysmogram form the user's skin. With all of the above-listed sensors, a proper contact with the user's skin improves the accuracy of the measurements and, as a consequence, the performance of such sensors may be improved with the above-described band 100, 300 when used to form-fit the band and a sensing head of the sensor to the user's skin. In some embodiments, the physical activity measurement device is connected to one or more biometric sensors 19 that are external to the casing. The external biometric sensor(s) 19 may be comprised in the band or they may be external to the apparatus. The processor 12 may communicate with the external biometric sensor(s) 19 in a wired or wireless manner. For example, a wiring may be provided between the processor 12 and the biometric sensor(s) 19 inside the band 10, or the casing 10 may comprise a wireless communication circuitry configured to communicate with a counterpart wireless communication circuitry of the biometric sensor(s) 19 according to a wireless communication protocol such as Bluetooth® or Bluetooth Smart.

The physical activity measurement device may comprise an electric interface 14 providing galvanic connection to the electrode(s) of the band 100, 300. Accordingly, the processor may control the provision of the electric input or stimuli to the electroactive material(s) provided in the band. The electric interface 14 may convert digital control signals or digital commands received from the processor 12 into electric voltages output to signal lines leading to the selected electrode(s) of the band, wherein the selection and the level of the electric voltage may be defined by the digital control signal received from the processor 12. Accordingly, the electric interface may comprise a circuitry converting the digital commands to the electric voltages and electric signal terminals connected to the signal lines leading to the electrode(s) of the band.

The physical activity measurement device may further comprise a user interface 24. The user interface 24 may comprise one or more user input devices in the form of one or more buttons and/or a touch-sensitive display. The user interface 24 may comprise one or more user output devices such as a display screen and/or a loudspeaker. In some embodiments, the electroactive material is employed as a user output device of the user interface 24. The electroactive material may be used to provide a haptic output.

As used in this application, the term 'circuitry' refers to all of the following: (a) hardware-only circuit implementations, such as implementations in only analogue and/or digital circuitry, and (b) to combinations of circuits and software (and/or firmware), such as (as applicable): (i) a combination of processor(s) or (ii) portions of processor(s)/software including digital signal processor(s), software, and memory (memories) that work together to cause an apparatus to perform various functions, and (c) to circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, an integrated circuit or applications processor integrated circuit for a physical activity measurement device.

In embodiments where the electroactive material is dielectric electroactive material and where the battery of the physical activity measurement device is not designed to provide a sufficient power supply to realize the voltage required to deform the electroactive material, the user may connect the physical activity measurement device to the external power supply, e.g. the USB, for the duration of the deformation of the electroactive material. In such an embodiment, upon determining to output the electric input to the electroactive material, the processor 12 may first check whether or not sufficient power supply is available, e.g. by checking whether or not the physical activity measurement device is currently connected to the external power supply. If the processor determines that the sufficient power supply is available, the processor 12 may cause the electric input to deform the electroactive material. On the other hand, if the processor 12 determines that the sufficient power supply is not available, the processor 12 may cause output of a notification through the user interface, wherein the notification may request the user to connect to the external power supply.

Let us now describe some applications employing the band structure described above. The embodiments described below with reference to FIGS. 9 to 14 may be carried out by the physical activity measurement device and controlled by the processor 12.

Figure 9:
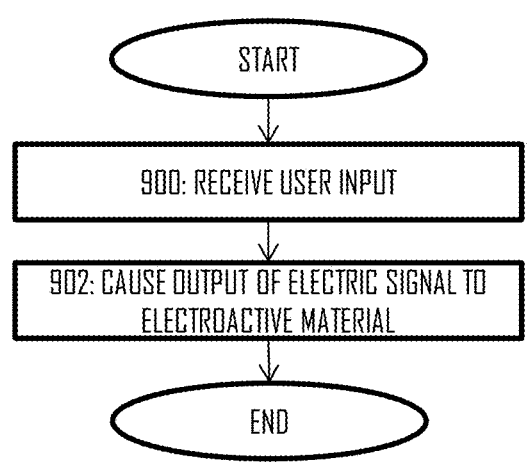
FIG. 9 illustrates a process for deforming the band in response to a user input according to an embodiment of the invention.

Referring to FIG. 9, the processor 12 may monitor the user interface 24. Upon detecting a user input through the user interface 24 in block 900, the processor 12 may decode the meaning of the user input from the context of the current state of the processor 12 and/or display content currently displayed to the user. Upon decoding the user input as a determined type of user input, the processor 12 may output a control signal to the electric interface 14 to output the electric input to the electroactive material. In response to the electric input, the electroactive material changes its size and shape. For example, the user may control the form-fitting of the band by inputting a user input command to the physical activity measurement device in order to change the form-fitting. The command may instruct the processor 12 to loosen or tighten form-fitting. In another example, the user may change the operational mode with the user input and, as a response, the processor 12 may determine to change the form-fitting parameters of the band 100.

Figure 10:
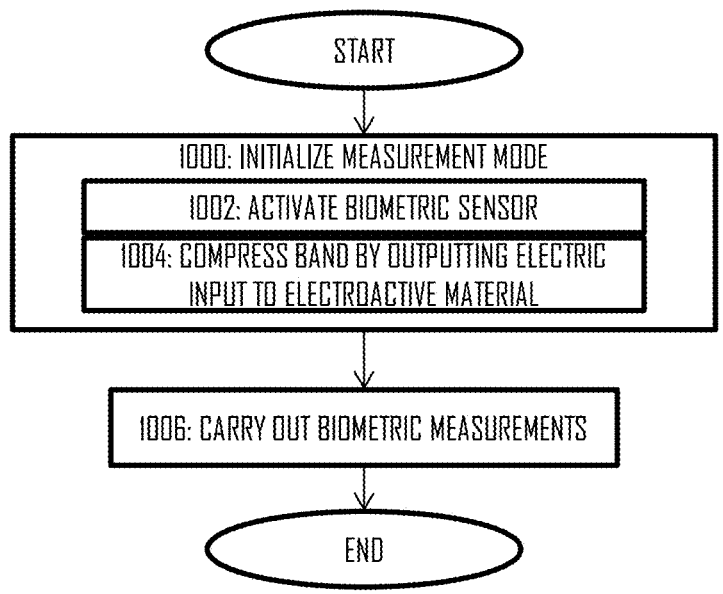
FIG. 10 illustrates a process for deforming the band upon starting a measurement mode according to an embodiment of the invention.

Referring to FIG. 10, the processor 12 may change the form-fitting parameters in response to a change in an operational mode of the physical activity measurement device. In the embodiment of FIG. 10, the operational mode changes from an idle mode to a measurement mode. In the idle mode, the sensor(s) controlled by the physical activity measurement device may be deactivated. Upon determining to change the operational mode to the measurement as a response to detection of a triggering event triggering the measurement mode, the processor 12 may initialize the measurement mode in block 1000. The triggering event may be reception of a user input through the user interface 24 or reception of an input from another device communicating with the physical activity measurement device. In block 1000, the processor may activate the biometric sensor(s) 18, 19 (block 1002) and change the form-fitting of the band (1004). In an embodiment, block 1004 comprises causing the band 100 to attach more firmly to the user's body by outputting the electric input to the electroactive material. The electroactive material may be configured to expand towards the user's body as a response to the electric input, thus realizing more firm form-fitting of the band 100 to the user's body. The technical effect is that the biometric sensor has a better contact with the user's skin and that the biometric sensor remains in contact with the skin even during the physical exercise, thus providing more accurate measurements.

Depending on the embodiment, block 1004 may comprise causing all the electroactive material in the band to expand or causing expansion only in the electroactive material in the area where a sensor head of the biometric sensor is located. In block 1006, the biometric measurements are performed 1006 by the biometric sensor(s) 18, 19 providing measurement signals and the processor 12 computing measurement data from the measurement signals. The processor 12 may apply one or more signal processing algorithms to convert the measurement signals provided by the biometric sensor(s) 18, 19 into digital measurement data.

Figure 11:
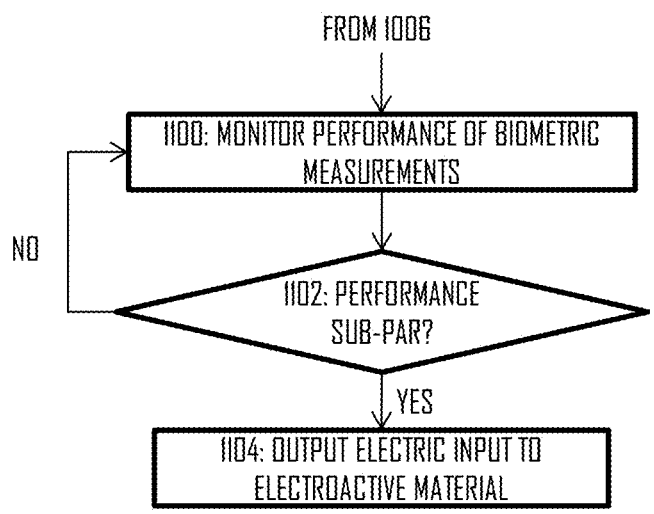
FIG. 11 illustrates an embodiment of the process of FIG. 10 where the deformation of the band is adjusted on the basis of performance of measurements.

Let us describe another embodiment for changing the form-fitting of the band 100 with reference to FIG. 11. Block 1006 may comprise monitoring the performance of the biometric measurements (block 1100). The monitoring may comprise determining whether or not the biometric measurements provide reasonable measurement results. For example, high variance in the measurement data or temporary unavailability of the measurement data may indicate poor performance resulting from sub-optimal contact between the sensor head and the skin. In block 1102, it is determined whether or not the performance of the biometric measurements is acceptable. If it is determined that the performance is acceptable, the no measures may be taken and the process may return to block 1100. On the other hand, if the processor 12 determines on the basis of said monitoring that the performance of the biometric measurements is sub-optimal, the processor may output a command to change the electric input applied to the electroactive material (block 1104). This results in a different form-fitting of the band. In an embodiment, the electric input applied in block 1104 may cause the electroactive material to expand and cause the band to grip more tightly to the user's body. In this manner, the processor 12 may adjust the form-fitting by applying different electric inputs to the electroactive material such that the optimal fitting is reached and, as a result, reliable measurements may be carried out.

In an embodiment, a criterion for determining whether or not the performance is acceptable in block 1102 is a received signal level of a measurement signal received from the biometric sensor(s). For example, an optical heart activity sensor may provide a higher level measurement signal when the sensor head is in proper contact with the user's skin than in a case where the contact is poor. Accordingly, if the signal level of the measurement signal is above a determined threshold, the performance may be acceptable. Otherwise, the performance may be determined unacceptable and the adjustment of the band fitting may be triggered.

Figure 12:
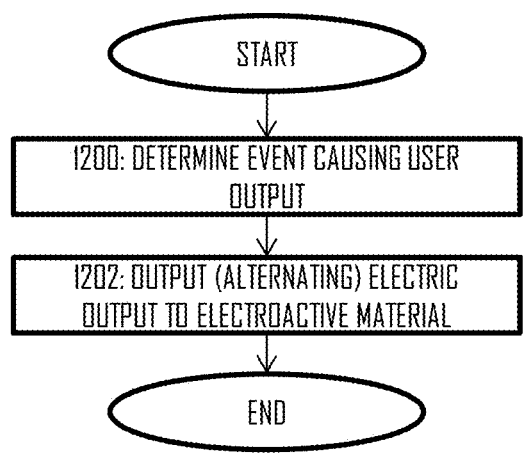
FIG. 12 illustrates a process for deforming the band in order to provide the user with a haptic output.

FIG. 12 illustrates a process for an embodiment where the processor uses the electroactive material to provide a haptic output to the user. Referring to FIG. 12, the processor may detect, during the measurement mode or during another operational mode, an event that causes an output of a notification or information to the user (block 1200). Upon determining that the event is of a type that triggers a haptic output, the processor 12 may output a signal causing electric input to the electroactive material (block 1202). In an embodiment, the electric input is an alternating input that causes a vibrating haptic output to the user.

Figure 13:
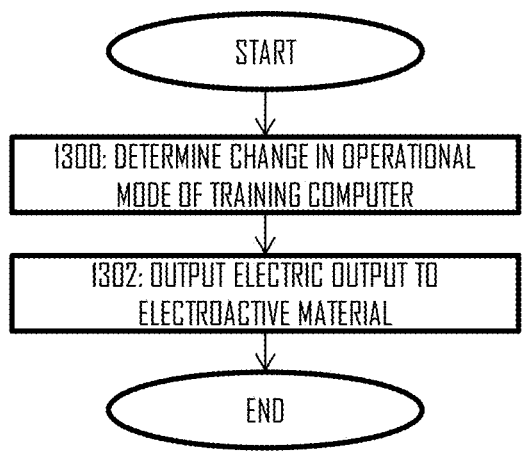
FIG. 13 illustrates a process for deforming the band in response to a change in an operational mode of the physical activity measurement device according to an embodiment of the invention.

FIG. 13 illustrates an embodiment where the processor 12 determines that the operational mode of the physical activity measurement device has changed (block 1300) and, in response to the determining, cause the electric input to the electroactive material (1302). Above, it has been described an embodiment where the operational mode changes from the idle mode to the measurement mode. Another example is a change from the idle mode to a calibrating mode in which the optimal form-fitting is calibrated (see the embodiment of FIG. 14 for the calibration mode). Another example is a change from the measurement mode to the idle mode in which case the processor 12 may control the electroactive material to loosen the grip from the user's body, thus providing more relaxed fitting of the band and the physical activity measurement device to the user's body.

Let us now describe some further embodiments for changing the form-fitting of the band to the user's body.

In an embodiment, the processor 12 causes the electric input to the electroactive material in response to detection of an event in acceleration measurement data received from an acceleration sensor comprised in the physical activity measurement device or in communication with the processor 12. For example, if the acceleration measurement data shows that the user is moving, the processor 12 may determine to improve the form-fitting and cause the electroactive material to expand and grip more tightly to the user's body. On the other hand if the acceleration measurement data shows that the user is staying still, the processor 12 may determine to loosen the form-fitting and cause the electroactive material to withdraw and relax the contact with the user's body. The processor 12 may control the electric input in proportion to the degree of movement: the higher the motion, the higher level of the electric input may be applied to the electroactive material, thus causing higher expansion of the electroactive material.

In an embodiment, the processor 12 causes the electric input to the electroactive material in response to detection that the band has been attached to the user's body. The detection may be based on measurements of a motion sensor, e.g. the acceleration sensor. The detection may be detecting of motion that represents motion of the human body. The detection may be based on an electric input from the attachment mechanism of the band. For example, the band may comprise a buckle and a catch, wherein a contact between the buckle and the catch causes an electric signal input to the physical activity measurement device to indicate that the band has been attached to the user's body.

In an embodiment, the band comprises a pressure sensor configured to measure the pressure the band causes to the user's skin. The pressure sensor may output its pressure measurement data to the processor 12. In response to the pressure measurement data, the processor may cause the electric input to the electroactive material. For example, if the pressure measurement data indicates no pressure or pressure below a determined threshold, the processor 12 may input a higher level electric input to the electroactive material to increase the pressure on the user's skin and to provide better contact. If the pressure measurement data indicates pressure above the determined threshold, the processor 12 may input a lower level electric input to the electroactive material to release the pressure on the user's skin.

In an embodiment, the processor 12 provides a personalized electric input to the electroactive material. The user may register to the physical activity measurement device by selecting his/her user profile through a user interface of the physical activity measurement device. In some embodiments, another device such as a personal computer or a smart phone connected to the physical activity measurement device is used as the user interface for selecting the user profile. In response to the selection of the user profile, the processor 12 may select form-fitting parameters associated with the user profile and apply electric input(s) corresponding to the form-fitting parameters according to any one of the above-described embodiments. Different users may have different form-fitting parameters because of different dimensions and shapes of the bodies.

Figure 14:
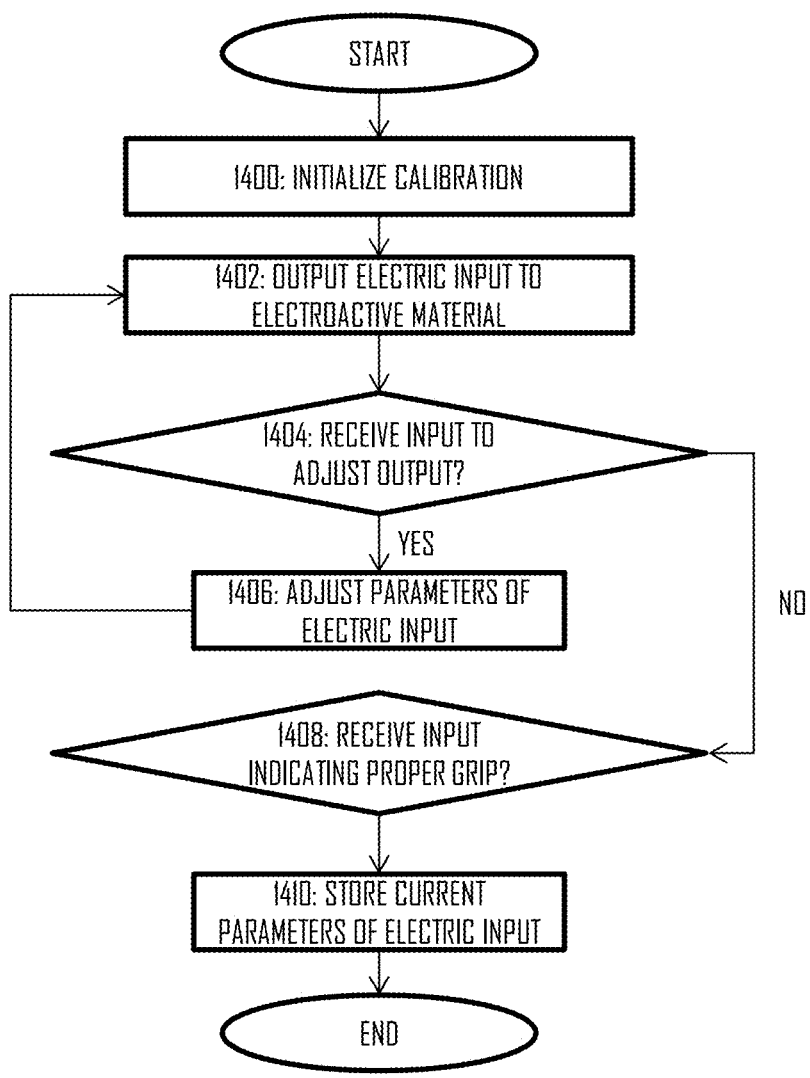
FIG. 14 illustrates a process for personalizing the deformation according to an embodiment of the invention.

FIG. 14 illustrates an embodiment of a calibration mode with which the personalized form-fitting may be realized. Referring to FIG. 14, the processor 12 may initialize the calibration in block 1400. In an embodiment, block 1400 comprises activating the above-described pressure sensor measuring the pressure of the band 100 to the object. In an embodiment, block 1400 comprises outputting a notification of the start of the calibration mode to the user, e.g. through the user interface 24. In an embodiment, block 1400 comprises verifying that the physical activity measurement device is connected to the external power supply, e.g. to a USB interface.

In block 1402, the processor causes the electric input to the electroactive material, thus causing the deformation of the electroactive material and the reduction in the effective inner circumference band 100. In block 1404, if the processor receives an input to adjust the fitting of the band, the processor proceeds to block 1406 where the processor adjusts the parameters of the electric input. The input may be an input from the pressure sensor or an input from the user. If the input indicates to increase the form-fitting, the processor may adjust the parameters such that a higher level electric input is applied to the electroactive material in block 1402 and/or that more electroactive material modules are stimulated with the electric input. On the other hand, if the input indicates to decrease the form-fitting, the processor may adjust the parameters such that a lower level electric input is applied to the electroactive material in block 1402 and/or that less electroactive material modules are stimulated with the electric input. Upon receiving an input indicating that the fitting of the band to the object is optimal in block 1408, the processor 12 may store the parameters defining the current electric input in the memory 20 (block 1410). The processor 12 may then use these parameters when applying the electric input to the electroactive material according to any one of the above-described embodiments.

The processes or methods described in FIGS. 2A to 8 may also be carried out in the form of a computer process defined by a computer program. The computer program may be in source code form, object code form, or in some intermediate form, and it may be stored in a transitory or a non-transitory carrier, which may be any entity or device capable of carrying the program. Such carriers include a record medium, computer memory, read-only memory, electrical carrier signal, telecommunications signal, and software distribution package, for example. Depending on the processing power needed, the computer program may be executed in a single electronic digital processing unit or it may be distributed amongst a number of processing units.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus comprising:
  a biometric sensor comprising a sensing head and arranged to measure biometric activity from skin of a human body;
  a band configured to place the sensing head in contact with the human body; and
  electroactive material comprised in the band, wherein the electroactive material is configured to change at least one of size and shape of the band in response to an electric input from the biometric sensor to the electroactive material such that the band fits the sensing head into tighter contact with the human body, wherein the electroactive material is attached to an inner surface of the band, the inner surface being configured to face the human body to which the band attaches a physical activity measurement device.

2. The apparatus of claim 1, wherein the electroactive material comprises electroactive polymers.

3. The apparatus of claim 2, wherein the electroactive polymers are dielectric electroactive polymers arranged to deform in response to the electric input and not requiring any electric input to maintain the deformation.

4. The apparatus of claim 1, wherein the electroactive material is arranged in a plurality of modules.

5. The apparatus of claim 4, wherein at least two of the modules of electroactive material are provided with independent control of the electric input.

6. The apparatus of claim 5, wherein at least some of the plurality of strips are arranged in parallel with respect to each other.

7. The apparatus of claim 4, wherein the electroactive material is arranged in a plurality of strips that extend along the band in a longitudinal direction of the band.

8. The apparatus of claim 1, wherein the electroactive change of the size and/or shape of the electroactive material in response to the electric signal causes a reduction in an effective circumference of the band.

9. The apparatus of claim 1, wherein the response of the electroactive material to the electric input causes the band to grip more tightly around a user's limb when attached to said limb.

10. An apparatus comprising:
  a biometric sensor comprising a sensing head and arranged to measure biometric activity from skin of a human body;
  a band configured to place the sensing head to in contact with the human body; and
  electroactive material comprised in the band, wherein the electroactive material is configured to change at least one of size and shape of the band in response to an electric input from the biometric sensor to the electroactive material such that the band fits the sensing head into tighter contact with the human body, wherein the electroactive material is arranged to change at least one of size and shape in a direction perpendicular to an inner surface of the band.

11. The apparatus of claim 10, wherein the electroactive material is arranged to bend.

12. An apparatus comprising:
  a biometric sensor comprising a sensing head and arranged to measure biometric activity from skin of a human body;
  a band configured to place the sensing head to in contact with the human body;

electroactive material comprised in the band, wherein the electroactive material is configured to change at least one of size and shape of the band in response to an electric input from the biometric sensor to the electroactive material such that the band fits the sensing head into tighter contact with the human body; and a physical activity measurement device comprising at least one electric power source and at least one processor, wherein the processor is configured to control output of the electric input from the biometric sensor to the electroactive material.

13. The apparatus of claim 12, wherein the processor is configured to output the electric input to the electroactive material upon receiving a user input through a user interface of the physical activity measurement device.

14. The apparatus of claim 12, further comprising a biometric sensor arranged to measure biometric activity from a skin of the human body, wherein the processor is configured to output the electric input to the electroactive material upon activating the biometric sensor.

15. The apparatus of claim 14, wherein the biometric sensor is an optical heart activity sensor configured to measure heart activity optically from a skin of the human body.

16. The apparatus of claim 14, wherein the processor is configured to output a first electric input to the electroactive material upon activating the biometric sensor and to output to the electroactive material during operation of the biometric sensor a second electric input different from the first electric input.

17. The apparatus of claim 16, wherein the processor is configured to determine performance of biometric measurements and output the second electric input in response to the determined performance.

18. The apparatus of claim 12, wherein the processor is configured to provide a user with a haptic output by outputting the electric input to the electroactive material.

19. The apparatus of claim 12, wherein the processor is configured to output the electric input to the electroactive material upon detecting a change in an operational mode of the physical activity measurement device.

20. The apparatus of claim 12, wherein the processor is configured to store, in a memory of the apparatus, parameters defining the electric input, wherein the parameters have been determined during a calibration phase in which the parameters have been determined on the basis of the dimensions of the human body to which the band is arranged to attach.

* * * * *